United States Patent [19]
Pohl et al.

[11] Patent Number: 4,776,855
[45] Date of Patent: Oct. 11, 1988

[54] HAIR DYEING PROCESS AND COMPOSITION

[75] Inventors: Stanley Pohl, Scarsdale; Michael Hnatchenko, Bronx, both of N.Y.

[73] Assignee: Clairol Inc., New York, N.Y.

[21] Appl. No.: 52,219

[22] Filed: May 18, 1987

Related U.S. Application Data

[63] Continuation of Ser. No. 841,404, Mar. 19, 1986, abandoned.

[51] Int. Cl.$^4$ ............................................... A61K 7/13
[52] U.S. Cl. ............................................ 8/406; 8/407; 8/410; 252/186.28
[58] Field of Search ............................ 8/406, 407, 410; 252/186.28

[56] References Cited

U.S. PATENT DOCUMENTS

| | | | |
|---|---|---|---|
| 3,884,627 | 5/1975 | Brody et al. | 8/10.2 |
| 4,130,501 | 12/1978 | Letz et al. | 252/186 |
| 4,311,478 | 1/1982 | Bugaut et al. | 8/407 |
| 4,313,932 | 2/1982 | Watts | 424/62 |
| 4,323,360 | 4/1982 | Bugaut et al. | 8/407 |
| 4,685,931 | 8/1987 | Schieferstein et al. | 8/406 |

FOREIGN PATENT DOCUMENTS 827331 2/1960 United Kingdom .

OTHER PUBLICATIONS

Rohm and Haas Company Brochure, "Acrysol ICS-1 Thickener for Use in Cosmetic and Toiletry Products", Aug. 1983.
Witiak, D., "A New High Efficiency Aqueous Thickener", *Happi*, Feb. 1983, pp. 56-60.
Witiak, David, "A High Efficiency Aqueous Thickener", CA98(20):166753W.
Balsam et al, *Cosmetics Science and Technology*, 2nd ed., vol. 2, Wiley Interscience, NY, 1973, p. 681.

*Primary Examiner*—Dennis Albrecht
*Assistant Examiner*—L. Skaling
*Attorney, Agent, or Firm*—Morton S. Simon

[57] ABSTRACT

A two part oxidation dyeing method for human hair is provided together with a composition therefor in which both parts are relatively fluid until mixed, after which the combination becomes viscous and can be applied to hair.

9 Claims, No Drawings

HAIR DYEING PROCESS AND COMPOSITION

This is continuing application of application Ser. No. 841,404, filed on Mar. 19, 1986, now abandoned.

BACKGROUND OF THE INVENTION

In dyeing of human hair with direct dyes as distinguished from oxidation dyes, the resultant final color is a combination of the natural hair color plus the color added by the dye. Where oxidation dyes are utilized and the hair is to be dyed a shade that is lighter than the shade of the person's hair, the dyeing procedure first eliminates the natural shade of the hair through bleaching with an oxidizing agent such as alkaline hydrogen peroxide. Then the desired shade is obtained on the hair by contacting it with the oxidation dye. Colored polymeric compounds of high molecular weight are produced on the hair by the action of atmospheric oxygen or by oxidizing agents such as hydrogen peroxide. It is also possible to simultaneously bleach and color the hair. In such cases hair is concurrently bleached by alkaline hydrogen peroxide as dyestuff penetrates into the hair and is oxidized to produce the desired color.

When oxidation dyes are used in the dyeing of human hair, the procedure usually involves the use of a two part system. One part is the lotion formulation which contains a variety of ingredients including the oxidation dye precursor chemicals which when mixed with the second part, the developer formulation, prior to application to the human head, causes the formation of the desired colored dyes. The developer usually contains an oxidizing agent such as hydrogen peroxide or a peroxide precursor. If sufficient peroxide is used, some of the natural melanin pigment of the hair may be destroyed first and the colored dyestuffs formed by oxidative coupling of the precursors in the first part, penetrate into the hair to give it the desired color. Such systems will generally contain 50% or more of organic solvents and surfactants, and require relatively high levels of dye to produce the desired color.

In practice surfactants are normally used to thicken the hair dye compositions to a more viscous consistency which will prevent the composition from running off the hair during use. The surfactants are dissolved in organic solvents. When the aqueous developer is added to the lotion, the water dilutes the organic solvents and the surfactants come out of solution and will thicken the composition.

It is also known from patents to use certain polymers in the developer to provide viscous solutions of hydrogen peroxide, however a number of well known cosmetic thickeners are not stable in hydrogen peroxide solutions. Furthermore, thickening of the solution is desirable only after the lotion and developer parts have been mixed together.

U.S. Pat. No. 4,130,501 discloses the use of various Carbopol resins for preparing thickened hydrogen peroxide formulations. These formulations were found to be stable when the solutions were made alkaline with sodium hydroxide. However, they are stable in storage only as thickened alkaline gels and are applied in that form.

U.K. patent No. 827,331 discloses the use of certain polymers, including copolymers of methacrylic acid, as thickeners for hydrogen peroxide in bleaching of hair. The formulations in the patent are described as thick gels over a pH range of 3 to 8 and are applied to hair in the thick condition. A thickened peroxide composition, such as is described in this reference would not be useful for oxidation dyes because it would be difficult to mix with the dye solution.

U.S. Pat. No. 4,313,932 discloses a dry, powder composition for admixture with water to provide a hair bleaching composition. The reference also discloses use of certain acrylic polymers to thicken peroxide formulations after water is added. The thickener used in this reference is part of the powder composition which is added to the peroxide immediately before use. Stability of the thickener to peroxide during storage is not a consideration as the product is a dry powder.

Several conditions are important for the procedures using oxidation dyes to work properly. First and foremost, stability of the formulations is imperative, particularly if the product is to be packaged and marketed. Secondly, mixing of the two parts should be quick and easy. Thirdly, after mixing, the resultant thickened solution should have the properties of being easily applied to the head and thick enough to remain on the hair until the dyeing process is complete and removal can take place.

Accordingly, it is an object of the present invention to provide a stable, oxidation dye formulation. It is a further object of the present invention to provide a two part dye composition which can be readily mixed and easily applied to the hair. It is still a further object of the present invention to provide an oxidation dye composition which is thick enough to remain on the hair until the dyeing process is complete. It is yet another object of this present invention to provide a two part dye composition containing substantially lower amounts of solvents, surfactants and dye than has generally been heretofore employed.

SUMMARY OF THE INVENTION

The present invention involves the use of a unique polymer for thickening hair treatment formulations. This material forms a stable fluid emulsion when maintained in aqueous solution or added to hydrogen peroxide. The formulation does not thicken until addition of an alkaline dye lotion immediately before application to the hair. Where a peroxide solution is employed, it is very important that the peroxide solution remain in a thin, fluid emulsion until mixed with the dye lotion to enable easy pouring and mixing. It has now been discovered that polymers of an ester of a $C_{16}$ to $C_{22}$ carboxylic acid and a polyalkylene glycol ether of a $C_{16}$ to $C_{22}$ alcohol and two or more monomers of $C_{16}$ to $C_{22}$ carboxylic acids or their esters are surprisingly stable to hydrogen peroxide and form thin emulsions therewith. Of these compounds it is most preferred to employ acrylates/steareth 20 methacrylate copolymer, [the nomenclature of the Cosmetic, Toiletry and Fragrance Association (CFTA), Cosmetic Ingredient Dictionary, Third Edtion Supplement, 1985] such as sold by Rohm & Haas, Philadelphia, Pa. as a cosmetic thickener under the trade name Acrysol-ICS. It was discovered that Acrysol ICS is most suprisingly stable to hydrogen peroxide and forms a thin emulsion therewith at neutral or acid pH. This copolymer is a polymer of an ester of methacrylic acid steareth 20 and two or more monomers consisting of acrylic acid, methacrylic acid or their simple esters. When a solution of Acrysol ICS is treated with an aqueous ammonia solution, having an alkaline pH in the range range normally associated with oxidation dyeing, and containing dyestuff precursors, the resulting mixture has a thickened viscosity which is suitable for hair dyeing. Very highly aqueous dye systems are very desirable.

DESCRIPTION OF THE INVENTION

The use of Acrysol-ICS is a key ingredient of the developer part of this invention when used in oxidative hair dye compositions. It is described as forming a thin emulsion at neutral or acid pH which thickens on neutralization above pH 7. Acrysol-ICS when added to hydrogen peroxide is suprisingly stable. When a solution of hydrogen peroxide containing at least 3% active Acrysol-ICS is brought to a pH which is within the alkaline pH range used in hair dyeing, by the addition of an alkalizer such as ammonia or alkanolamine, the resulting mixture has a thickened viscosity which is suitable for dyeing purposes. No organic surfactant or solvent need be present, although in practice some small amounts of surfactants or solvents would probably be needed to help dissolve the dyes and provide foaming and conditioning. Very highly aqueous oxidation dye systems are very desirable. The oxidation hair dye bases of the present invention whose compositions are given below contain only about 5% organic solvents and surfactants as compared with 50% or more in current products. There are a number of advantages of such high water content dye systems. Aside from the obvious cost saving, it was found that dyeing is much more efficient when solvents and surfactants are kept to a minimum; about one half as much dye is needed to produce the same shade as in current products. Also, it is likely that there will be less skin and scalp staining by dye in a more highly aqueous system, partly because the low concentration of surfactants washes away less of the protective oil in the skin. Furthermore, the thickened solution is quite thixotropic, spreading easily into the hair but showing excellent "stay-put" quality when the shear is removed.

Adding of about 1% based on the hair dye composition of an aqueous solution of Acryol-ICS to the developer prior to mixing the lotion and the developer, enables the tailoring of the viscosity of the ultimate hair dyeing composition. Thus, for example, a hair dresser can add Acrysol-ICS to a more fluid hair dye composition suitable for use by a consumer and thus make it sufficiently viscous e.g. for root dyeing that is known to require a condsiderbly more viscous dye composition.

Although developer formulations containing Acrysol-ICS and hydrogen peroxide are suprisingly stable, it is sometimes advantageous to add known stabilizers for peroxide to the formulations to counteract the effect of impurities which could catalyze peroxide decomposition. Examples of substances which are known to stabilize hydrogen peroxide are phenacetin, EDTA and other substances which complex heavy metal ions such as are disclosed in U.S. Pat. Nos. 3,378,444 and 3,632,295.

Typical preferred compositions prepared in accordance with the present invention will contain a lotion part (Part A) having a pH of about 8 to 12 and containing the oxidation hair dye intermediate or intermediates, and a developer part (Part B), the latter containing from about 0.04% to about 25% by weight of Acrysol-ICS and 1% to 10% of hydrogen peroxide maintained at a pH of about 1.5 to 5.5. If desired, the primary components of Part B, i.e., the Acrysol-ICS and the hydrogen peroxide can be maintained separately and combined just prior to mixing Part B with Part A, such as when the tailoring of the viscosity of the hair dye composition is carried out.

In addition to dyes, the lotion (Part A) can contain 0 to 20% hexylene glycol or propylene glycol which acts as a solvent, 0 to 20% Carbitol [2-(2-ethoxyethoxy)ethanol ethanol, or diethylene glycolmonoethylether] which acts as a solvent, 0 to 10% ammonia (28%) which acts as an alkalizer-thickener, 0 to 10% ammonium chloride which acts as a pH control and provides a buffering effect, 0 to 10% sodium lauryl sulfate (30%) which acts as a surfactant and 0 to 10% sodium chloride which assists in viscosity control, with the remainder being water.

In addition to the Acrysol-ICS and the hydrogen peroxide, the developer (Part B) can contain 0 to 0.2% phenacetin which acts as a stabilizer and 0 to 0.1% ethylene diamime tetraacetic acid (EDTA) which acts as a stabilizer, with the remainder being water. All percentages set forth in this specification, unless otherwise indicated, expressed are percent by weight.

A most preferred composition contains in Part A, in addition to dyes, 2% hexylene glycol, 4% Carbitol, 5.77% ammonia (28%), 2.84% ammonium chloride, 2% sodium lauryl sulfate (30%), 0.2% sodium chloride, made up to 100% with water. Part B of such preferred composition contains 10% Acrysol-ICS, 12.3% hydrogen peroxide (50%) and 0.04 phenacetin and 0.02% EDTA made up to 100% with water.

EXAMPLES 1-24

The six formulations of the lotion (Part A) were mixed in all possible combinations with the four formulations of the developer (Part B).

The following lotion formulations (Part A) are prepared:

|  | 1 | 2 | 3 | 4 | 5 | 6 |
|---|---|---|---|---|---|---|
| p-phenylenediamine | 0.3 | 0.4 | 0.05 | — | 0.5 | 0.5 |
| bishydroxylethyl-ppd sulfate | 0.05 | — | 0.05 | — | — | — |
| p-aminophenol | 0.1 | 0.2 | — | 0.4 | — | — |
| resorcinol | 0.4 | 0.5 | — | 0.2 | 0.5 | 0.5 |
| 1-naphthol | 0.05 | — | 0.05 | 0.05 | 0.01 | 0.01 |
| sodium sulfite | 0.1 | 0.1 | 0.1 | 0.1 | 0.1 | 0.1 |
| bentone LT | 0.4 | — | — | 0.2 | — | — |
| propylene glycol | 3.0 | — | 3.0 | 0.5 | 2.0 | — |
| hexylene glycol | — | — | — | — | — | 2.0 |
| carbitol | 4.0 | — | 2.0 | 3.0 | 2.0 | 4.0 |
| ammonia (28%) | 6.0 | 4.0 | 6.0 | 2.0 | — | 5.77 |
| ammonium chloride | 3.0 | 3.0 | 1.5 | 2.0 | 2.0 | 2.84 |
| sodium lauryl sulfate | — | — | 4.0 | — | — | 2.0 |
| sodium chloride | — | 3.0 | — | — | — | 0.2 |
| ethanolamine | — | — | — | — | 6.0 | — |
| ethanolamine hydrochloride | — | — | — | — | 4.0 | — |
| fragance | — | — | — | — | — | 0.1 |
| water (to 100%) |  |  |  |  |  |  |

The following developer formulation (Part B) are prepared:

|  | A | B | C | D |
|---|---|---|---|---|
| Acrysol ICS-1 | 12.0 | 10.0 | 6.0 | 10.0 |
| hydrogen peroxide (50%) | 12.3 | 10.0 | 12.0 | 12.3 |
| phenacetin | — | 0.04 | — | 0.02 |
| EDTA | — | 0.02 | 0.02 | — |
| water (to 100%) |  |  |  |  |

All combinations of Part A and Part B are mixed (Examples 1–24) and applied to human hair. The viscosities of these formulations after mixing are all in the range of 2000–12000 cps. The hair is dyed to varying shades of blonde or brown except for combinations containing lotion #2 which tones hair to a blue-violet hue.

Viscosity measurements, made with a Haake Rotovisco Apparatus on one of the above combinations (Part A, #6 mixed with Part B, #2) illustrate the thixothropy exhibited by the system. Results are shown below:

| Shear Rate/ sec | Viscosity cps | Shear Stress Dynes/sq cm |
|---|---|---|
| 8.5 | 4372.2 | 162.0 |
| 16.9 | 2662.0 | 450.2 |
| 25.4 | 1838.0 | 466.3 |
| 50.7 | 982.4 | 498.5 |
| 76.1 | 718.3 | 546.7 |
| 152.2 | 422.5 | 643.2 |
| 228.3 | 309.9 | 707.5 |
| 456.7 | 172.5 | 787.9 |
| 685.0 | 145.5 | 997.0 |
| 1370.0 | 82.2 | 1125.6 |
| 1370.0 | 79.8 | 1093.4 |
| 685.0 | 138.5 | 948.7 |
| 456.7 | 186.6 | 852.2 |
| 228.3 | 316.9 | 723.6 |
| 152.2 | 433.1 | 659.3 |
| 76.1 | 802.8 | 611.0 |
| 50.7 | 1077.5 | 546.7 |
| 25.4 | 1901.4 | 482.4 |
| 16.9 | 2757.0 | 466.3 |
| 8.5 | 4753.5 | 402.0 |

What is claimed is:

1. A two part composition for hair treating when combined, wherein the two parts are intended to be admixed with each other shortly before use, which comprises
   (a) an aqueous first part containing an alkaline material in an amount sufficient to provide a final pH of about 8 to 12 when admixed with a second part; and
   (b) an aqueous second part containing about 0.04 to 25% by weight of a polymer of an ester of a $C_{16}$ to $C_{22}$ carboxylic acid and a polyalkylene glycol ether of a $C_{16}$ to $C_{22}$ alcohol and two or more monomers of $C_{16}$ to $C_{22}$ carboxylic acid or their esters, and 1 to 10% by weight of a peroxide at a pH of about 1.5 to 5.5.

2. The composition according to claim 1 wherein said polymer is acrylates/steareth 20 methacrylate copolymer and said peroxide is hydrogen peroxide.

3. The two part hair treating composition according to claim 2 wherein the first part further contains a tinctorially effective amount of an oxidation hair dye intermediate.

4. The composition according to claim 2 wherein said second part is combined just prior to mixing with said first part from two sub-parts, one containing the acrylate/steareth 20 methacrylate copolymer and the other the hydrogen peroxide.

5. The composition according to claim 3 wherein the first part further contains an amount of a solvent sufficient to solubilize the hair dye intermediate up to about 20%; said solvent selected from the group consisting of hexylene glycol, propylene glycol, diethylene glycolmonoethyl ether and mixtures of two or more thereof, and said second part further contains 0 to about 0.2% phenacetin, and 0 to about 0.1% EDTA.

6. The composition according to claim 2 wherein said first part contains 2% hexylene glycol, 4% diethyleneglycolmonoethyl ether, 5.77% ammonia (28%) 2.84% ammonium chloride, 2% sodium lauryl sulfate (30%), and 0.2% sodium chloride.

7. The composition according to claim 2 wherein said second part contains 10% acrylates/streareth-20 methacrylate copolymer, 12.3% hydrogen peroxide (50%), and 0.04% phenacetin and 0.02% EDTA.

8. A method for oxidation dyeing of human hair comprising admixing an aqueous lotion containing a tinctorially effective amount of an oxidation hair dye intermediate, and an alkaline material in an amount sufficient to provide a final pH of about 8 to 12 when admixed with an aqueous developer; and an aqueous developer containing about 0.04 to 25% by weight of a polymer of an ester of a $C_{16}$ to $C_{22}$ carboxylic acid and a polyalkylene glycol ether of a $C_{16}$ to $C_{22}$ alcohol and two or more monomers of $C_{16}$ to $C_{22}$ carboxylic acid or their esters, and 1 to 10% by weight of a peroxide at a pH of about 1.5 to 5.5; the lotion and the developer being thin emulsions which upon said admixing thicken to produce a thickened emulsion; then applying the thickened emulsion to the hair for a period of time sufficient for the dyeing process to take place.

9. The method according to claim 8 wherein the aqueous developer contains an aqueous emulsion of hydrogen peroxide and acrylates/steareth-20 methacrylate copolymer.

* * * * *